United States Patent
Göttsche et al.

(10) Patent No.: US 12,023,502 B2
(45) Date of Patent: Jul. 2, 2024

(54) EXTERNAL ELECTROMEDICAL PULSE GENERATOR

(71) Applicant: OSYPKA AG, Rheinfelden-Baden (DE)

(72) Inventors: Thorsten Göttsche, Mulhouse (FR); Benjamin Burg, Rheinfelden (DE)

(73) Assignee: OSYPKA AG, Rheinfelden-Baden (DE)

( * ) Notice: Subject to any disclaimer, the term of this patent is extended or adjusted under 35 U.S.C. 154(b) by 78 days.

(21) Appl. No.: 17/574,658

(22) Filed: Jan. 13, 2022

(65) Prior Publication Data
US 2022/0218982 A1   Jul. 14, 2022

(30) Foreign Application Priority Data
Jan. 14, 2021  (DE) .............. 10 2021 100 681.3

(51) Int. Cl.
*A61N 1/362* (2006.01)
*A61N 1/04* (2006.01)

(52) U.S. Cl.
CPC ......... *A61N 1/3625* (2013.01); *A61N 1/0492* (2013.01)

(58) Field of Classification Search
CPC .............. A61N 1/3625; A61N 1/0492
USPC ............................................. 607/2
See application file for complete search history.

(56) References Cited

U.S. PATENT DOCUMENTS

| 2012/0109254 A1 | 5/2012 | King |
| 2016/0067474 A1 | 3/2016 | Muessig et al. |
| 2017/0239483 A1 | 8/2017 | Mathur et al. |
| 2017/0361091 A1* | 12/2017 | Tai ............... A61N 1/37264 |

FOREIGN PATENT DOCUMENTS

DE    10 2017 111 280 A1    11/2018

OTHER PUBLICATIONS

Deutsches Patent—und Markenamt; Official Summons Date of hearing: Mar. 5, 2024; Issued Date Jan. 12, 2023 and English translation.
Deutsches Patent—und Markenamt; Addition to Summons for file numbers; Date of hearing: Mar. 5, 2024; Issued Date Jan. 12, 2023 and English translation.

* cited by examiner

*Primary Examiner* — Nadia A Mahmood
(74) *Attorney, Agent, or Firm* — Grogan, Tuccillo & Vanderleeden LLP

(57) ABSTRACT

The invention relates to improvements in the technical field of external electromedical pulse generators. For this purpose, it is proposed in the case of an electromedical pulse generator that it has an electronics module and a control module separate therefrom, which can be used spatially separated from one another when the electromedical pulse generator is used.

10 Claims, 2 Drawing Sheets

EXTERNAL ELECTROMEDICAL PULSE GENERATOR

CROSS REFERENCE

Figure 1:
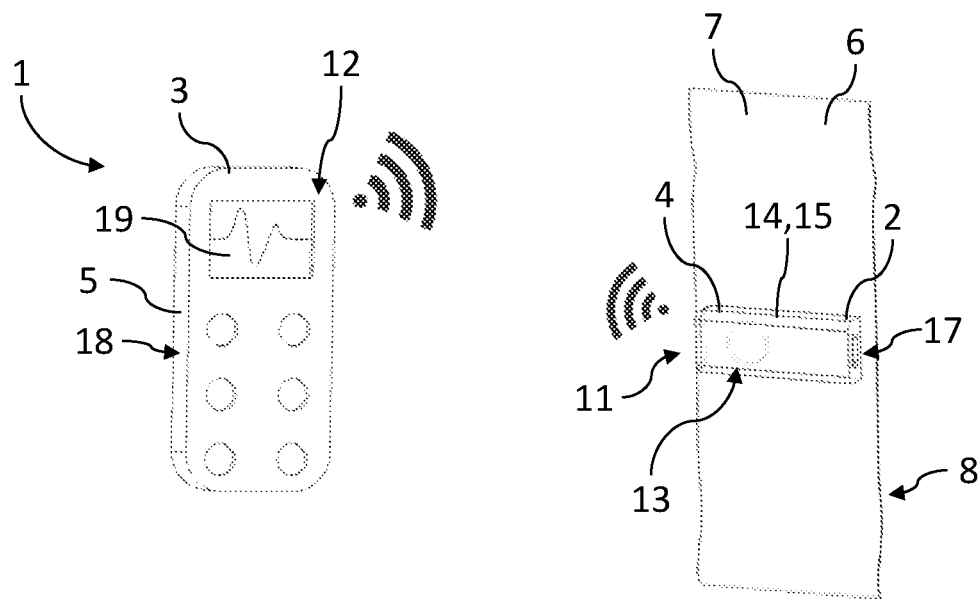

This application claims priority to German Patent Application No. 10 2021 100 681.3, filed on Jan. 14, 2021, all of which is hereby incorporated by reference in its entirety.

BACKGROUND

The invention relates to an external electromedical pulse generator.

Such external electromedical pulse generators are used, for example, as external cardiac pacemakers to support the cardiac function in patients after medical interventions. Stimulation pulses can be delivered from outside the body to the target tissue of the patient with the external pulse generator via an electromedical electrode, which is placed into a target tissue of a patient transcutaneously and/or through a body opening. As soon as the patient is no longer dependent on the external stimulation by the external pulse generator, the electromedical electrode can be withdrawn and the pulse generator removed.

The object of the invention is to provide an external electromedical pulse generator which is characterized by especially simple and convenient handling.

SUMMARY

In order to achieve the object, an external electromedical pulse generator is proposed which has the means and features of the independent claim. Thus, in order to achieve the object, particularly an external electromedical pulse generator is proposed having an electronics module and a control module for controlling or reading out the electronics module, the electronics module and the control module being separate modules. The electronics module in this case can be configured to deliver stimulation pulses and/or possibly also to record electromedical body signals and/or physiological parameters, for example physiological body signals, and/or biosignals.

Physiological parameters and/or biosignals can be, for example, inflammation parameters that can be detected with a corresponding sensor of the pulse generator. Physiological parameters can also be, for example, acceleration values, which can be measured with a corresponding acceleration sensor that the electromedical pulse generator can have. In this way, it is possible to infer a function of the monitored target tissue from an acceleration of a target tissue, for example a myocardial wall.

Because the electronics module, on the one hand, and the control module for the electronics module, on the other hand, are independent and separate modules, a common housing, in which both the electronics module and the control module for the electronics module are integrated as is common with previous external electromedical pulse generators, can be dispensed with. This makes it possible to use the electronics module and the control module of the external electromedical pulse generator spatially separated from one another. For example, the electronics module can remain on the patient, while the control module can be arranged and used independently thereof and spaced apart therefrom.

In a preferred embodiment of the pulse generator, it is provided that the electronics module and the control module each have their own housing and/or are spatially separated from each other in the position of use of the electromedical pulse generator. As already mentioned above, it is thus possible to leave the communication module, which can be used to deliver stimulation pulses to the target tissue of the patient, on the patient and to separate it spatially from the control module of the pulse generator.

By separating the two functional units, the control module and the electronics module of the pulse generator, it is possible, in particular, to make the housing of the electronics module comparatively small. Thus, the electronics module can be left on the patient without this being disruptive for the patient. The separation of the functional units of the electromedical pulse generator also favors the miniaturization thereof, which can further simplify the handling of the pulse generator in comparison to the comparatively large external electromedical pulse generators that have been typically used previously.

In an especially preferred embodiment of the pulse generator, it is provided that the electronics module, in particular the housing thereof, is connected to an adhesive plaster or is thereby stuck to the skin. With the aid of the adhesive plaster, the electronics module can be stuck to the outside of the body of a person to be treated with the pulse generator. In this case, the electronics module can be arranged on an outer side of the adhesive plaster that faces away from an adhesive side of the adhesive plaster. In another embodiment of the pulse generator, the electronics module is arranged on an adhesive side of the adhesive plaster.

Through the connection of the electronics module to the adhesive plaster and the possibility of miniaturizing the electronics module, which is possible due to the structure according to the invention of the external electromedical pulse generator, the part of the external electromedical pulse generator, namely the electronics module, which can be configured for delivering stimulation pulses and/or for recording electromedical or other physiological body signals or body states or for recording physiological parameters and/or biosignals, can be attached directly to the person to be treated. In this way, the part of the external electromedical pulse generator relevant for stimulating and/or recording electromedical body signals can be arranged in an especially space-saving manner. Any impairment of medical personnel due to the arrangement of the electromedical pulse generator can thus be largely avoided or even completely prevented.

In one embodiment of the pulse generator, the electronics module and the control module and/or a recording module can have corresponding communication interfaces for communication amongst one another. In this way, it is possible to transmit the control commands required for controlling the electronics module from the control module to the electronics module. Conversely, it is also possible, for example, to transmit electromedical or other physiological or biological body signals or body states and/or physiological parameters and/or biosignals recorded with the aid of the electronics module to the control module and/or to the recording module, via the communication interface of the electronics module, and to process them there, in particular to evaluate and/or to output and/or to store them.

It is especially advantageous if the communication interface of the electronics module and of the control module are wireless communication interfaces. In this way, there is no need for cabling between the electronics module and the control module. This can considerably simplify the handling of the electromedical pulse generator. Cables that are routed from the patient to a part of the pulse generator, namely, for example, to the control module in order to operate the external pulse generator, can be dispensed with here.

In order to operate the electronics module of the pulse generator wirelessly, it is useful if the electronics module has a power source, for example a battery and/or an accumulator. The power source can enable delivery of a stimulation pulse to a muscle and/or a nerve without a wired connection of the electronics module to an external power source.

It can also be advantageous for the use of the electronics module to record electromedical body signals if the electronics module has the aforementioned power source. It is also possible to use the power source of the electronics module to effect preferably wireless communication to the control module via the communication interface of the electronics module.

As mentioned above, it is advantageous if the pulse generator is also configured for recording electromedical body signals, particularly by means of the electronics module thereof and/or by means of the control module thereof. In this way, the delivery of stimulation pulses can take place as a function of the recorded, electromedical and/or other physiological and/or biological body signals and/or of physiological parameters and/or of biosignals.

The electronics module of the pulse generator can have a stimulation module for the delivery of stimulation pulses. The stimulation module can be configured to trigger stimulation pulses as a function of recorded electromedical body signals.

The electronics module of the pulse generator can have a recording module for recording electromedical body signals. Both the stimulation module and the recording module can be connected to the aforementioned communication interface of the pulse generator in order, on the one hand, to transfer recorded electromedical body signals and/or physiological parameters and/or biosignals from the electronics module to the outside, for example to the previously mentioned control module or to another evaluation unit. On the other hand, it is also possible to use the control module to transmit corresponding trigger signals and/or programming data to the electronics module and the stimulation module and/or the recording module of the electronics module.

The electronics module can be connected to an electromedical electrode. In this way, it is possible, with the aid of the electronics module, to deliver stimulation pulses, via the electromedical electrode, to a target tissue of a person equipped with the pulse generator. It is also possible to use the electromedical electrode to transmit electromedical body signals from a patient to the electronics module, in particular to the patient's recording module, and to provide them therein for further processing and/or transmission, for example, to the control module of the pulse generator.

It is especially advantageous if the electromedical electrode is an electrode made of printed circuit board foil. Such an electrode can be produced especially easily and inexpensively and provided with the desired contacts and/or circuits.

In order to record and/or measure said physiological parameters and/or biosignals, the pulse generator can have at least one corresponding sensor, for example a biosensor and/or an acceleration sensor and/or a temperature sensor and/or a pH value sensor, and/or at least one electromedical contact pole. The at least one sensor and/or the at least one electromedical contact pole can be arranged and/or formed on an electrode, for example on the aforementioned electromedical electrode. If necessary, stimulation pulses from the pulse generator can be delivered to the target tissue via the at least one contact pole.

The control module can have a user interface for operating and/or programming the electronics module. Corresponding inputs for operating and/or programming the electronics module and any further modules that may be present, such as the previously mentioned stimulation module and/or the aforementioned recording module, can be entered and transmitted from the control module to the electronics module via the user interface.

The electronics module can have a connection interface for connecting an electromedical electrode. In one embodiment of the electronics module, the connection interface is designed as a plug socket.

The invention will subsequently be described in more detail using an exemplary embodiment but is not limited to this exemplary embodiment. Further exemplary embodiments result from the combination of features of individual or several claims with one another and/or in combination with individual or several features of the exemplary embodiment.

DRAWINGS

Figure 2:
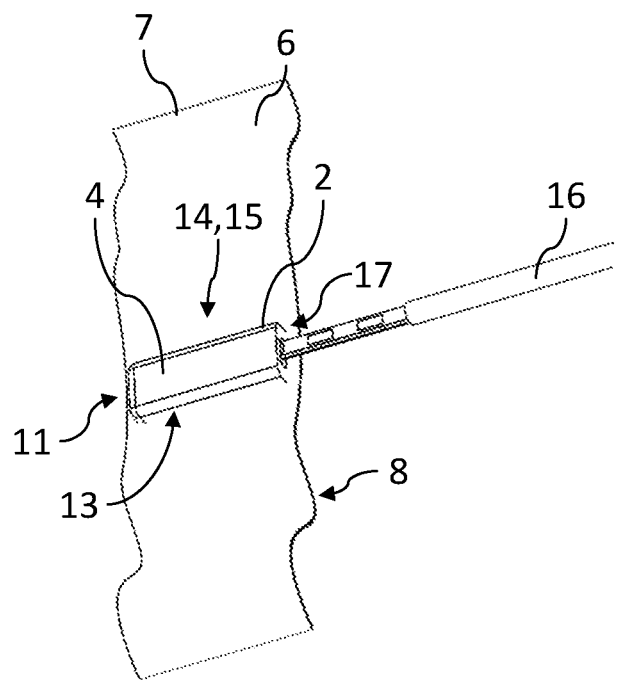
Figure 3:
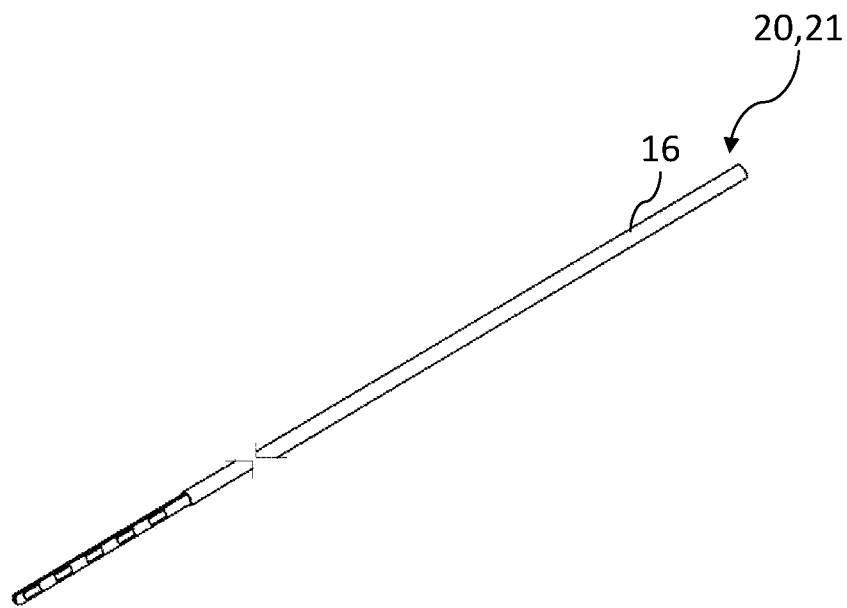
Figure 4:
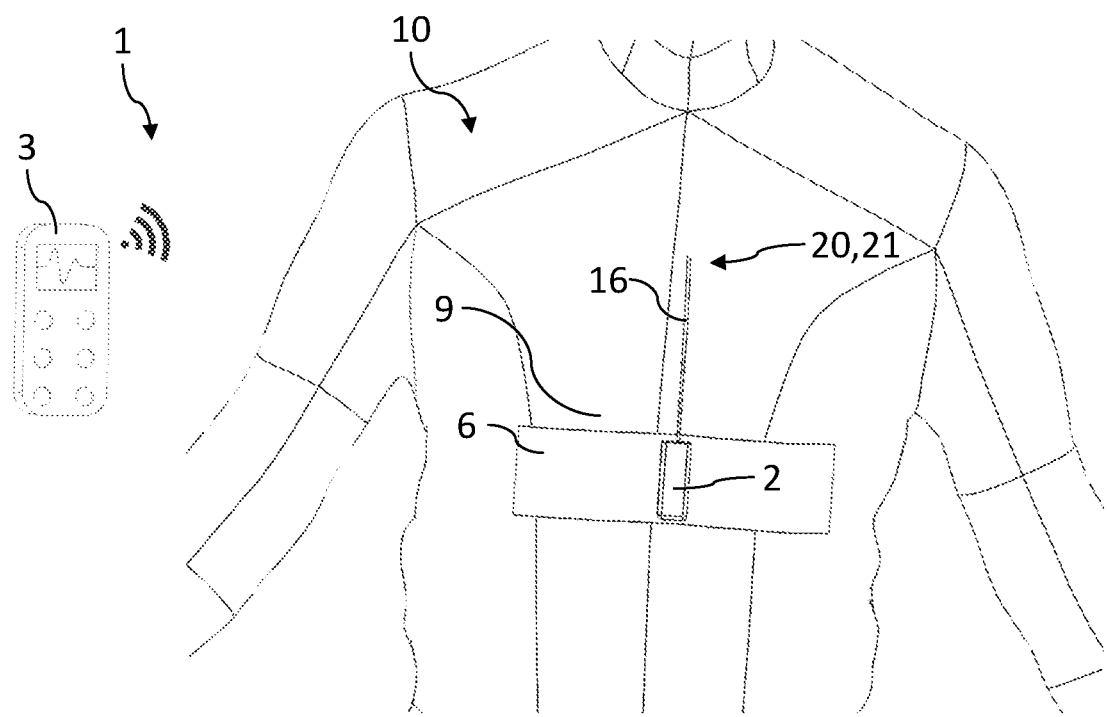

The drawings show the following:

FIG. 1 a perspective view of an external electromedical pulse generator, in which the pulse generator has a control module and an electronics module, which have their own housing and are configured for wireless communication with one another, as separate and spatially separated modules;

FIG. 2 a perspective view of the electronics module shown in FIG. 1 with an electromedical electrode, just before connection to the electronics module, and an adhesive plaster, which is connected to the housing of the electronics module;

FIG. 3 a perspective view of the electromedical electrode of the pulse generator; and FIG. 4 an illustration of the electromedical pulse generator in the position of use on a patient.

DETAILED DESCRIPTION

All figures show at least parts of an external electromedical pulse generator designated as a whole by 1. According to FIG. 1, the electromedical pulse generator 1 has an electronics module 2, which is configured to deliver stimulation pulses and to record electromedical body signals, and a control module 3 for controlling the electronics module 2.

The electronics module 2 and the control module 3 are separate and spatially separated modules in the position of use of the electromedical pulse generator 1.

Both the electronics module 2 and the control module 3 each have their own housings, 4 and 5, which allow the spatially separated arrangement and use of the electronics module 2 and the control module 3.

FIGS. 1, 2, and 4 show that the electronics module 2 is connected to an adhesive plaster 6. The adhesive plaster 6 is arranged on the housing 4 of the electronics module 2 and connected thereto. The electronics module 2 is specifically arranged on an outer side 7 of the adhesive plaster 6 which faces away from an adhesive side 8 of the adhesive plaster 6.

FIG. 4 makes it clear that the electronics module 2 can be attached, with the aid of the adhesive plaster 6, to the outside of a body 9 of a person 10 to be treated with the pulse generator 1.

The electronics module 2 and the control module 3 have corresponding communication interfaces, 11 and 12, which enable communication between the two modules, 2 and 3. Communication interfaces 11 and 12 are wireless communication interfaces and therefore enable wireless communication between the electronics module 2 and the control module 3. FIG. 1 shows that the electronics module 2 has a power source 13 in the form of a battery or an accumulator. In this way, the electronics module 2 can be operated independently of an external power source to which the electronics module 2 would otherwise have to be connected via a power line. As already mentioned above, the pulse generator 1 is configured for recording electromedical body signals, in particular by the electronics module 2.

The electronics module 2 has a stimulation module 14 for delivering stimulation pulses and a recording module 15 for recording electromedical body signals and/or physiological parameters and/or biosignals. The electronics module 2 of the electromedical pulse generator 1 can be connected to an electromedical electrode 16 according to FIGS. 2 and 4. The electromedical electrode 16 can consist, for example, at least partially of printed circuit board foil.

According to FIGS. 3 and 4, at least one sensor 20 and at least one electromedical contact pole 21 are arranged in the distal end region of the electrode 16. Physiological parameters of the patient and/or biosignals of the patient can be detected via the at least one sensor 20. An acceleration sensor, a biosensor, a pH value sensor, and/or a temperature sensor can be used, for example, as the sensor 20. For example, inflammatory states of the target tissue can be detected with a biosensor.

Electromedical body signals of the target tissue can be detected via the at least one contact pole 21. If necessary, stimulation pulses can also be delivered from the stimulation module 14 of the pulse generator 1 to the target tissue of the person 10 via the at least one contact pole 21.

To connect the electromedical electrode 16, the electronics module 2 has a connection interface 17 in the form of a plug socket. The plug socket can be seen clearly in FIGS. 1 and 2. The control module 3 of the pulse generator 1 has a user interface 18 for operating and programming the electronics module 2 and the stimulation module 14 thereof and the recording module 15 thereof. Part of the user interface 18 of the control module 3 is a display 19 via which the relevant information can be output. Data and information derived from the recorded body signals and/or physiological parameters and/or biosignals of the person 10 being treated with the external electromedical pulse generator 1 can also be shown on the display 19.

The external electromedical pulse generator 1 shown in the figures is designed as an external cardiac pacemaker and can be used temporarily, for example, to support the cardiac function of a patient.

The invention relates to improvements in the technical field of external electromedical pulse generators. For this purpose, it is proposed in the case of an electromedical pulse generator 1 that it has an electronics module 2 and a control module 3 separate therefrom, both of which can be used spatially separated from one another when the electromedical pulse generator 1 is used.

What is claimed is:

1. An external electromedical pulse generator comprising:
    an electronics module for delivering stimulation pulses, recording electromedical body signals, physiological parameters and/or biosignals;
    a control module for controlling the electronics module; and
    wherein the electronics module and the control module are separate modules;
    wherein the electronics module is connected to an electromedical electrode;
    wherein the electromedical electrode, in a use position of the pulse generator, is laid transcutaneously and/or through a body opening into a target tissue of a patient.

2. The pulse generator according to claim 1, wherein the electronics module and the control module each have their own housing and/or are spatially separated from each other.

3. The pulse generator according to claim 2, wherein the housing of the electronics module is attached to an adhesive side of an adhesive plaster or to an outer side of the adhesive plaster, which faces away from the adhesive side of the adhesive plaster.

4. The pulse generator according to claim 1, wherein the electronics module and the control module have corresponding wireless communication interfaces for communication with one another.

5. The pulse generator according to claim 1, wherein the electronics module includes a battery or an accumulator as a power source.

6. The pulse generator of claim 1, wherein the pulse generator wherein the electronics module and/or the control module is configured to record electromedical body signals.

7. The pulse generator of claim 1, wherein the electronics module has a stimulation module for delivering stimulation pulses and/or a recording module for recording electromedical body signals.

8. The pulse generator of claim 1, wherein the pulse generator has at least one sensor and/or at least one electromedical contact pole for detecting electromedical body signals, physiological parameters, and/or biosignals; and
    wherein the at least one sensor and the at least one electromedical contact pole is arranged on the electromedical electrode of the pulse generator.

9. The pulse generator of claim 1, wherein the electronics module has a connection interface for connecting an electromedical electrode.

10. The pulse generator of claim 1, wherein the control module has a user interface for operating the stimulation module and/or the recording module.

* * * * *